US007247287B2

(12) United States Patent
Cao et al.

(10) Patent No.: US 7,247,287 B2
(45) Date of Patent: *Jul. 24, 2007

(54) SYNTHESIS OF ALUMINOPHOSPHATES AND SILICOALUMINOPHOSPHATES

(75) Inventors: Guang Cao, Branchburg, NJ (US); Matu J. Shah, Livingston, NJ (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/459,204

(22) Filed: Jun. 11, 2003

(65) Prior Publication Data

US 2004/0253163 A1    Dec. 16, 2004

(51) Int. Cl.
 *C01B 37/08* (2006.01)
(52) U.S. Cl. .............................. 423/306; 423/DIG. 30; 502/214
(58) Field of Classification Search ................ 502/208, 502/214; 423/305, 306, 327.1, DIG. 30
See application file for complete search history.

(56) References Cited

U.S. PATENT DOCUMENTS

| | | | | |
|---|---|---|---|---|
| 4,310,440 | A | 1/1982 | Wilson et al. | 252/435 |
| 4,440,871 | A | 4/1984 | Lok et al. | 502/214 |
| 4,503,023 | A | 3/1985 | Breck et al. | 423/328 |
| 4,786,487 | A | 11/1988 | Kuehl | 423/306 |
| 4,861,739 | A | 8/1989 | Pellet et al. | 502/64 |
| 5,096,684 | A | 3/1992 | Guth et al. | 423/306 |
| 6,001,328 | A | 12/1999 | Lillerud et al. | 423/718 |
| 6,162,415 | A | 12/2000 | Liu et al. | 423/706 |
| 6,620,983 | B1 * | 9/2003 | Cao et al. | 585/640 |
| 6,680,278 | B2 * | 1/2004 | Cao et al. | 502/214 |
| 6,793,901 | B2 * | 9/2004 | Cao et al. | 423/305 |
| 2004/0089001 | A1 * | 5/2004 | Kakiuchi et al. | 62/112 |
| 2004/0093876 | A1 * | 5/2004 | Inagaki et al. | 62/112 |
| 2005/0009691 | A1 * | 1/2005 | Cao et al. | 502/214 |

FOREIGN PATENT DOCUMENTS

| | | |
|---|---|---|
| CN | 1067633 | 6/1993 |
| EP | 0 103 117 | 3/1984 |
| EP | 293 939 | 7/1988 |
| EP | 0 324 082 | 7/1989 |
| EP | 0 391 774 | 10/1990 |
| EP | 993 867 | 9/2000 |
| FR | 2 682 944 | 4/1993 |
| JP | 59-217619 | * 12/1984 |
| WO | WO 97/33692 | 9/1997 |
| WO | WO 98/15496 | 4/2000 |
| WO | WO 01/36328 | 5/2001 |
| WO | 02/066910 | 8/2002 |

OTHER PUBLICATIONS

Liu et al., New Insights into the Crystallization Mechanism of Microporous AIPO4-211, Microporous and Mesoporous Materials, vol. 22, pp. 33-41 (1998).

Pluth et al., Silicoaluminophosphate with Encapsulated Methylbutylamine Species: Chabazite Structure, Charge Coupling Between Framework and Inferred Ammonium Species, and Severe Molecular Disorder, J.Phys.Chem., vol. 93, pp. 6516-6520, (1989).

McKie et al., "Essentials of Crystallography", Blackwell Scientific Publications, p. 89 (1986).

E. H. Halvorsen, "Synthesis and Characterization of Aluminophosphate Molecular Sieve" Ph.D. Thesis, University of Oslo, (1996).

Feng et al., Amine-directed Syntheses and Crystal Structures of Phosphate-based Zeolite Analogs, Microporous and Mesoporous Materials, vol. 23, pp. 221-229 (1998).

H. Kessler, Synthesis in the Presence if Fluoride High-Silica Zeolites, Aluminophosphates and Derived Materials, Microporous Materials, vol. 22 pp. 517-518, (1998).

Kwon et al., "Synthesis of Mesoporous Molecular Sieves Hydrolysis of H2SiF6 by a Non-ionic Polyethyleneoxide Surfactant Template," Microporous and Mesoporous Materials, vol. 27 pp. 255-259 (1999).

Harding et al., Microcrystal Structure Determination of AIPO4-CHA Using Synchrotron Radiation, Acta Cryst., vol. C50, pp. 852-854, (1994).

Meier et al., "Atlas of Zeolite Framework Types," Fifth Revised Edition, p. 96-97 (2001).

Prakash et al., Synthesis and Characterization of SAPO-5 Molecular Sieve Using N, N-dimethylbenzylamine as Template, Microporous Materials, vol. 2, pp. 83-89, (1994).

Vistad et al., "Multinuclear NMR Analysis of Sapo-34 Gels in the Presence and Absence of HF: The Initial Gel", *Journal of Physical Chemistry A.*, 103, pp. 2540-2552 (1999).

Wilson et al., "The Characteristics of SAPO-34 which Influence the Conversion of Methanol to Light Oelfins," *Microporous and Mesoporous Materials*, vol. 29, pp. 117-126, (1999).

MicroPatent PatSearch Fulltext—"English Abstract of WO 02/066910—priority document for 2004/0089011, already of record", No date.

* cited by examiner

*Primary Examiner*—David Sample
(74) *Attorney, Agent, or Firm*—David M. Weisberg; Frank E. Reid (57) ABSTRACT

The invention is directed to a method of synthesising silicoaluminophosphate and aluminophosphate molecular sieves using synthesis templates that contain at least one template of general formula $R^1R^2N—R^3$, wherein $R^1$ and $R^2$ are independently selected from the group consisting of alkyl groups having from 1 to 3 carbon atoms and hydroxyalkyl groups having from 1 to 3 carbon atoms; $R^3$ is selected from the group consisting of 4- to 8-membered cycloalkyl groups, optionally substituted by 1 to 3 alkyl groups having from 1 to 3 carbon atoms, and 4- to 8-membered heterocyclic groups having from 1 to 3 heteroatoms, said heterocyclic groups being optionally substituted by 1 to 3 alkyl groups having from 1 to 3 carbon atoms and the heteroatoms in said heterocyclic groups being selected from the group consisting of O, N, and S. In particular, the present invention relates to the synthesis of silicoaluminophosphate molecular sieves of the CHA framework type having a low silicon to aluminium atomic ratio.

24 Claims, 3 Drawing Sheets

SYNTHESIS OF ALUMINOPHOSPHATES AND SILICOALUMINOPHOSPHATES

FIELD OF INVENTION

This invention relates to the synthesis of silicoaluminophosphate and aluminophosphate molecular sieves of the CHA framework type. In particular the present invention relates to the synthesis of silicoaluminophosphate molecular sieves of the CHA framework type having a low silicon to aluminium atomic ratio.

BACKGROUND OF THE INVENTION

Olefins are traditionally produced from petroleum feedstock by catalytic or steam cracking processes. These cracking processes, especially steam cracking, produce light olefin(s) such as ethylene and/or propylene from a variety of hydrocarbon feedstock. It has been known for some time that oxygenates, especially alcohols, e.g. methanol, are convertible into light olefin(s). The preferred methanol conversion process is generally referred to as a methanol-to-olefin(s) process, where methanol is converted to primarily ethylene and propylene in the presence of a molecular sieve.

Some of the most useful molecular sieves for converting methanol to olefin(s) are the metalloaluminophosphates such as the silicoaluminophosphates (SAPO's). There are a wide variety of SAPO molecular sieves known in the art, of these the more important examples include SAPO-5, SAPO-11, SAPO-18, SAPO-34, SAPO-35, SAPO-41, and SAPO-56. For the methanol-to-olefins process SAPO molecular sieves having the CHA framework and especially SAPO-34 are particularly important catalysts. The CHA framework type has a double six-ring structure in an ABC stacking arrangement. The pore openings of the structure are defined by eight member rings that have a diameter of about 4.0 Å, and cylindrical cages within the structure of approximately 10×6.7 Å ("Atlas of Zeolite Framework Types", 2001, 5th Edition, p. 96). Other SAPO molecular sieves of CHA framework type include SAPO-44, SAPO-47 and ZYT-6.

The synthesis of SAPO molecular sieves is a complicated process. There are a number of variables that need to be controlled in order to optimise the synthesis in terms of purity, yield and quality of the SAPO molecular sieve produced. A particularly important variable is the choice of synthesis template, which usually determines which SAPO framework type is obtained from the synthesis. U.S. Pat. No. 4,310,440 (Wilson et al.) teaches that "not all templating agents suitably employed in the preparation of certain species . . . are suitable for the preparation of all members of the generic class." It is also well known that the same template may induce the formation of different framework types.

In U.S. Pat. No. 4,440,871 (Lok et al.), the synthesis of a wide variety of SAPO materials of various framework types is described with a number of specific examples. Also disclosed are a large number of possible organic templates, with some specific examples. In the specific examples a number of CHA framework type materials are described. The preparation of SAPO-34 is reported, using tetraethylammonium hydroxide (TEAOH), or isopropylamine, or mixtures of TEAOH and dipropylamine (DPA) as templates. Also disclosed is a specific example that utilizes cyclohexylamine in the preparation of SAPO-44. Although other template materials are described, there are no other templates indicated as being suitable for preparing SAPO's of CHA framework type.

Since the synthesis of SAPO-34 was reported in U.S. Pat. No. 4,440,871, tetraethylammonium hydroxide (TEAOH) either alone, or in combination with dipropylamine (DPA), has been the preferred template for preparing SAPO-34. However, there are problems associated with the use of TEAOH and DPA. When used alone, TEAOH affords a limited range of synthesis parameters. For example, under certain conditions TEAOH will also template the synthesis of SAPO-18 which has the AEI framework type. TEAOH is thus relatively intolerant to synthesis condition variations. TEAOH is sometimes combined with DPA. However, DPA has a low boiling point (110° C.) resulting in the need for production plants that can handle high pressures. In certain countries, the use of DPA requires special regulatory authorizations due to its toxicity. Also, DPA is an aggressive template and is often implicated in re-dissolution of the silicoaluminophosphate molecular sieve during its synthesis, resulting in poor quality crystalline product due to surface pitting of the crystals. Finally, it has proved difficult up to now to make pure phase CHA silicoaluminophosphate molecular sieves with a low silicon to aluminium atomic ratio.

In U.S. Pat. No. 4,440,871, it was reported that SAPO-44 was obtained "as the major phase" using cyclohexylamine as a template. In U.S. Pat. No. 6,162,415 (Liu, et al.), relatively pure CHA SAPO-44 was obtained using the same template but with control of the ratio of template to aluminium source and the ratio of phosphorous source to aluminium source.

In European Patent Publication No. EP 0 993 867, it was reported that the use of methylbutylamine resulted in SAPO-47 and the use of cyclohexylamine resulted in impure SAPO-44. Methylbutylamine has an even lower boiling point, at 91° C., than DPA.

In U.S. Pat. No. 4,861,739 (Pellet, et al.), Example 102, it was reported that the use of N,N-diethylethanolamine produced CoAPSO-47 having Si concentrated on the peripheries of the crystal and Co at the center.

In U.S. Pat. No. 4,310,440 (Wilson et al.), triethanolamine, N,N-dimethylethanolamine, N,N-diethylethanolamine, N-methyldiethanolamine, and N-methylethanolamine, were all used to prepare $AlPO_4$-5, aluminophosphates of framework type AFI. N-methylethanolamine was also reported to produce $AlPO_4$-21 of framework type AWO.

In European Patent Publication No. EP 0 993 867, it was reported that diethanolamine produced SAPO-34 and SAPO-5 under different synthesis conditions.

In the art various attempts have been made to improve the synthesis of $AlPO_4$ or SAPO molecular sieves. One approach has been the addition of a source of fluoride ions to the synthesis mixture.

In U.S. Pat. No. 5,096,684 (Guth et al.), morpholine and tetraethylammonium hydroxide were found to template the production of SAPO-34 when in the presence of HF. According to Guth et al., the use of HF in combination with the organic template results in silicoaluminophosphates which have improved thermal and hydrolytic stability.

In U.S. Pat. No. 4,786,487 (Kuehl et al.), SAPO-20 was produced from synthesis mixtures containing tetramethylammonium hydroxide and fluoride ions from water soluble sources of fluoride such as Na, K and ammonium fluoride.

In U.S. Pat. No. 6,001,328 (Lillerud et al.), a silicoaluminophos-phate indicated as UiO-S7 was prepared using tetramethylammonium hydroxide pentahydrate or tetramethylammonium hydroxide, in combination with HF.

In a Ph.D. thesis (E. H. Halvorsen, University of Oslo, 1996), it was reported that low silica SAPO-34, designated as UiO-S4, was produced using TEAOH template in combination with HF.

Wilson et al., reported that it is beneficial to have lower Si content for methanol-to-olefins reaction (Microporous and Mesoporous Materials, 29, 117-126, 1999). Low Si content has the effect of reducing propane formation and decreasing catalyst deactivation.

As can bee seen from the disclosures described herein, there have been a number of attempts to utilize alternative synthesis templates for the CHA framework type, with limited success. It is desirable therefore to find new synthesis templates that are specific for the synthesis of silicoaluminophosphate or aluminophosphate molecular sieves of CHA framework type. It is also desirable to find new templating systems which afford more effective control of the final composition of silicoaluminophosphates of CHA framework types and in particular control of the Si/Al (silicon to aluminium atomic) ratio in the final product. In molecular sieves of CHA framework type, the Si/Al atomic ratio is often expressed as the number of Si atoms per CHA cage of the molecular sieve, each CHA cage being composed of 12 T atoms (T atoms are either Si, Al or P). It is also desirable to find templates suitable under a wide range of molecular sieve synthesis conditions for the synthesis of silicoaluminophosphate or aluminophosphate molecular sieves of CHA framework type.

SUMMARY OF THE INVENTION

The present invention provides a process for preparing crystalline molecular sieve of CHA framework type, which process comprises;
(a) providing a synthesis mixture comprising a source of aluminum, a source of phosphorus, a source of silicon and at least one organic template of formula (I)

$$R^1R^2N-R^3 \quad (I)$$

wherein $R^1$ and $R^2$ are independently selected from the group consisting of alkyl groups having from 1 to 3 carbon atoms and hydroxyalkyl groups having from 1 to 3 carbon atoms;

$R^3$ is selected from the group consisting of 4- to 8-membered cycloalkyl groups, optionally substituted by 1 to 3 alkyl groups having from 1 to 3 carbon atoms, 4- to 8-membered heterocyclic groups having from 1 to 3 heteroatoms, said heterocyclic groups being optionally substituted by 1 to 3 alkyl groups having from 1 to 3 carbon atoms and the heteroatoms in said heterocyclic groups being selected from the group consisting of O, N, and S; and b) inducing crystallization of crystalline molecular sieve of CHA framework type from the reaction mixture.

Preferably, the organic template of formula (I) is a template of formula (II)

$$(CH_3)_2N-R^3 \quad (II)$$

wherein $R^3$ is a 4- to 8-membered cycloalkyl groups, optionally substituted by 1 to 3 methyl groups.

More preferably, the organic template is selected from the group consisting of N,N-dimethyl-cyclohexylamine, N,N-dimethyl-methyl-cyclohexylamine, N,N-dimethyl-cyclopentylamine, N,N-dimethyl-methyl-cyclopentylamine, N,N-dimethyl-cycloheptylamine, N,N-dimethyl-methylcycloheptylamine. Most preferably, the organic template is N,N-dimethyl-cyclohexylamine.

The process of the present invention results molecular sieves having the CHA framework type which, as synthesized, have unique x-ray diffraction patterns.

In one embodiment of the present invention there is provided a silicoaluminophosphate molecular sieve, substantially of CHA framework type, comprising within its intra-crystalline structure at least one template of formula I, preferably of formula II, more preferably N,N-dimethyl-cyclohexylamine.

In a further embodiment the present invention provides a crystalline silicoaluminophosphate molecular sieve substantially of CHA framework type, having a characteristic X-ray powder diffraction pattern containing at least the d-spacings as set forth in Table Ia:

TABLE Ia

| 2 θ | d (A) | I % |
|---|---|---|
| 9.46 | 9.34 | 63 |
| 12.86 | 6.88 | 12 |
| 13.98 | 6.33 | 16 |
| 16.02 | 5.53 | 51 |
| 17.80 | 4.98 | 24 |
| 20.62 | 4.30 | 100 |
| 22.42 | 3.96 | 11 |
| 25.02 | 3.56 | 36 |
| 25.96 | 3.43 | 16 |
| 30.68 | 2.91 | 37 |
| 31.18 | 2.87 | 18 |

Preferably, the present invention provides a crystalline silicoaluminophosphate molecular sieve substantially of CHA framework type, having a characteristic X-ray powder diffraction pattern containing at least the d-spacings as set forth in Table Ib:

TABLE Ib

| 2 θ | d (A) | I % |
|---|---|---|
| 9.46 | 9.34 | 63 |
| 12.86 | 6.88 | 12 |
| 13.98 | 6.33 | 16 |
| 16.02 | 5.53 | 51 |
| 17.80 | 4.98 | 24 |
| 19.06 | 4.65 | 2 |
| 20.62 | 4.30 | 100 |
| 22.06 | 4.03 | 8 |
| 22.42 | 3.96 | 11 |
| 23.10 | 3.85 | 7 |
| 25.02 | 3.56 | 36 |
| 25.96 | 3.43 | 16 |
| 27.72 | 3.22 | 4 |
| 28.26 | 3.16 | 4 |
| 29.62 | 3.01 | 4 |
| 30.68 | 2.91 | 37 |
| 31.18 | 2.87 | 18 |
| 31.68 | 2.82 | 2 |
| 32.44 | 2.76 | 2 |
| 33.62 | 2.66 | 3 |
| 34.60 | 2.59 | 8 |
| 35.02 | 2.56 | 1 |
| 36.18 | 2.48 | 5 |
| 38.76 | 2.32 | 1 |
| 39.84 | 2.26 | 3 |
| 42.98 | 2.10 | 3 |
| 43.58 | 2.08 | 3 |
| 45.28 | 2.00 | 1 |
| 46.92 | 1.93 | 1 |
| 47.84 | 1.90 | 4 |
| 49.02 | 1.86 | 4 |
| 49.52 | 1.84 | 1 |

It is preferred that the molecular sieve having the X-ray diffraction pattern of Table Ia or Ib comprises N,N-dimethylcyclohexylamine within its intra-crystalline structure.

In another embodiment, the present invention provides a crystalline silicoaluminophosphate molecular sieve substantially of CHA framework type, having a characteristic X-ray powder diffraction pattern containing at least the d-spacings as set forth in Table IIIa:

TABLE IIIa

| 2 θ | d (A) | I % |
|---|---|---|
| 9.54 | 9.26 | 100 |
| 14.04 | 6.30 | 20 |
| 15.68 | 5.64 | 15 |
| 16.08 | 5.51 | 57 |
| 17.88 | 4.96 | 25 |
| 18.00 | 4.92 | 27 |
| 20.68 | 4.29 | 76 |
| 21.22 | 4.18 | 21 |
| 25.04 | 3.55 | 32 |
| 25.44 | 3.50 | 20 |
| 26.00 | 3.42 | 10 |
| 30.74 | 2.91 | 22 |
| 31.04 | 2.88 | 26 |
| 31.18 | 2.87 | 19 |

Preferably, the present invention provides a crystalline silicoaluminophosphate molecular sieve substantially of CHA framework type, having a characteristic X-ray powder diffraction pattern containing at least the d-spacings as set forth in Table IIIb:

TABLE IIIb

| 2 θ | d (A) | I % |
|---|---|---|
| 9.54 | 9.26 | 100 |
| 12.92 | 6.85 | 9 |
| 13.36 | 6.62 | 4 |
| 14.04 | 6.30 | 20 |
| 14.56 | 6.08 | 3 |
| 15.68 | 5.64 | 15 |
| 16.08 | 5.51 | 57 |
| 16.80 | 5.27 | 8 |
| 17.88 | 4.96 | 25 |
| 18.00 | 4.92 | 27 |
| 20.68 | 4.29 | 76 |
| 21.22 | 4.18 | 21 |
| 22.12 | 4.02 | 7 |
| 22.60 | 3.93 | 8 |
| 23.18 | 3.83 | 4 |
| 25.04 | 3.55 | 32 |
| 25.44 | 3.50 | 20 |
| 26.00 | 3.42 | 10 |
| 26.26 | 3.39 | 3 |
| 27.00 | 3.30 | 3 |
| 28.28 | 3.15 | 4 |
| 30.36 | 2.94 | 9 |
| 30.74 | 2.91 | 22 |
| 31.04 | 2.88 | 26 |
| 31.18 | 2.87 | 19 |
| 31.60 | 2.83 | 9 |
| 33.64 | 2.66 | 3 |
| 34.60 | 2.59 | 5 |
| 36.24 | 2.48 | 5 |
| 43.02 | 2.10 | 4 |

It is preferred that the molecular sieve having the X-ray diffraction pattern of Table IIIa or IIIb comprises N,N-dimethylcyclohexylamine within its intra-crystalline structure and fluoride, more preferably hydrogen fluoride.

In another embodiment the present invention provides a method for the manufacture of a molecular sieve catalyst composition, which method comprises forming a mixture comprising at least one molecular sieve of the present invention, with at least one formulating agent, to form a molecular sieve catalyst composition.

In yet a further embodiment the present invention provides for a molecular sieve catalyst composition comprising at least one molecular sieve of the present invention in admixture with at least one formulating agent.

In a further embodiment the present invention provides for the use of a template of formula I, preferably of formula II, more preferably N,N-dimethylcyclohexylamine, optionally in the presence of a source of fluoride, in the synthesis of silicoaluminophosphates of CHA framework type.

In another embodiment the present invention provides a method for the manufacture of a molecular sieve catalyst composition, which method comprises forming a mixture comprising at least one molecular sieve comprising within its intra-crystalline structure at least one template of formula I, preferably of formula II, more preferably N,N-dimethylcyclohexylamine, or as obtained from a process utilising a template of formula I, preferably of formula II, more preferably N,N-dimethylcyclohexylamine, with at least one formulating agent, to form a molecular sieve catalyst composition.

In yet a further embodiment the present invention provides for a molecular sieve catalyst composition comprising at least one silicoaluminophosphate molecular sieve comprising within its intra-crystalline structure at least one template of formula I, preferably of formula II, more preferably N,N-dimethylcyclohexylamine or as obtained from a process utilising a template of formula I, preferably of formula II, more preferably N,N-dimethylcyclohexylamine, in admixture with at least one formulating agent.

The molecular sieves of the present invention or prepared according to the preparation method of the present invention are useful catalysts for the conversion of feedstocks, preferably oxygenate feedstocks, into one or more olefins.

DETAILED DESCRIPTION

Introduction

The invention provides a method for synthesising crystalline aluminophosphates and silicoaluminophosphates substantially of the CHA framework type. In particular it has been found that a specific group of organic amines are effective templates in the synthesis of aluminophosphate and silicoaluminophosphate molecular sieves of the CHA framework type. It has been found that if templates of formula (I), preferably of formula (II), most preferably, N,N-dimethylcyclohexylamine, as described below are used to prepare SAPO molecular sieves, then SAPOs of CHA framework type and of substantially high purity are obtained. Furthermore, in another embodiment, these templates may be utilised for the synthesis of SAPOs of CHA framework type having low Si/Al atomic ratios, i.e. low acidity.

Molecular Sieves

The molecular sieves of the present invention, may be represented by the empirical formula, on an anhydrous basis:

$$mR:(Si_xAl_yP_z)O_2$$

wherein R represents at least one templating agent of formula (I)

$$R^1R^2N{-}R^3 \qquad (I)$$

wherein $R^1$ is selected from the group consisting of alkyl groups or hydroxyalkyl groups;

$R^2$ is selected from the group consisting of alkyl groups or hydroxyalkyl groups;

$R^3$ is selected from the group consisting of cycloalkyl groups having from 4 to 8 carbon atoms, said cycloalkyl groups being optionally substituted by 1 to 3 alkyl groups, 4 to 8-membered heterocyclic groups having 1 to 3 heteroatoms, said heterocyclic groups being optionally substituted by 1 to 3 alkyl groups and the heteroatoms in said heterocyclic groups being selected from the group consisting of O, N, and S, all alkyl and alkoxy groups independently having from 1 to 3 carbon atoms; and m is the number of moles of R per mole of $(Si_xAl_yP_z)O_2$ and m has a value from 0.0417 to 0.3333, preferably from 0.0624 to 0.166, and most preferably from 0.0667 to 0.1; x, y, and z respectively represent the mole fraction of Si, Al and P as tetrahedral oxides.

In one embodiment, m is greater than or equal to 0.04, x is greater than or equal to 0, and y and z are greater than or equal to 0.01. In another embodiment, m is in the range of from greater than 0.01 to about 0.3333, x is in the range of from greater than 0 to about 0.31, y is in the range of from 0.25 to 1.0, and z is in the range of from 0.25 to 0.9, more preferably m is in the range of from 0.05 to 0.10, x is in the range of from 0.01 to 0.2, most preferably from 0.02 to 0.15, y is in the range of from 0.4 to 0.9, and z is in the range of from 0.3 to 0.9. Optionally, the molecular sieve may also contain fluorine.

When the molecular sieves are calcined the organic template is removed and the resulting aluminophosphates or silicoaluminophosphates have a CHA framework type and are of substantially high purity in terms of their framework type with little or no intergrowth with other silicoaluminophosphate or aluminophosphate framework types. In the present specification when reference is made to a silicoaluminophosphate substantially of CHA framework type or of substantially high purity in terms of its framework type it is meant a silicoaluminophosphate molecular sieve which comprises 60% or greater of the CHA framework type, preferably 70% or greater of the CHA framework type, more preferably 90% or greater of the CHA framework type, and most preferably 95% or greater of the CHA framework type, as determined by XRD.

The molecular sieves of the present invention may contain a small amount of intergrowth with another silicoaluminophosphate or aluminophosphate molecular sieve. The molecular sieve can comprise at least one intergrown phase of AEI and CHA framework types. For example, SAPO-18, AlPO$_4$-18 and RUW-18 have an AEI framework type. In a further embodiment the molecular sieve may comprise a mixture of intergrown material and non-intergrown materials.

In one embodiment, the calcined molecular sieve of the present invention has a Si/Al ratio of less than 0.167, preferably less than 0.134, more preferably less than 0.100. In a preferred embodiment the Si/Al ratio in the molecular sieve is within the range of from 0 to 0.167, more preferably in the range of from 0.02 to 0.167, even more preferably in the range of from 0.03 to 0.134 and most preferably in the range of from 0.03 to 0.100.

Molecular Sieve Synthesis

Generally, silicoaluminophosphate and aluminophosphate molecular sieves are synthesized by the hydrothermal crystallization of one or more of a source of aluminium, a source of phosphorous, a templating agent (or template), and, optionally, a source of silicon. Typically, in the method of the present invention a combination of a source of aluminium, a source of phosphorous, one or more templating agents, optionally a source of silicon, and, optionally, one or more metal containing compounds are placed in a sealed pressure vessel, optionally lined with an inert plastic such as polytetrafluoroethylene, and heated, under a crystallization pressure and temperature, until a crystalline material is formed, and then recovered by filtration, centrifugation and/or decanting.

In a typical synthesis of the silicoaluminophosphate molecular sieve of the invention, the phosphorous-, aluminium-, and optionally silicon-containing components are mixed, preferably while stirring and/or agitating and/or seeding with a crystalline material, optionally with an alkali metal, in a solvent such as water, and one or more templating agents, to form a synthesis mixture that is then heated under crystallization conditions of pressure and temperature as described in U.S. Pat. Nos. 4,440,871 which is fully incorporated by reference.

In the process of the present invention, the template is used in an amount such that the molar ratio of template to alumina (Al$_2$O$_3$) in the reaction mixture is within the range of from 0.6:1.0 to 3.0:1.0, preferably from 1.0:1.0 to 2.0:1.0.

The templates used in the process of the present invention have the general formula (I)

$$R^1R^2N{-}R^3 \qquad (I)$$

wherein $R^1$ is selected from the group consisting of alkyl groups or hydroxyalkyl groups;

$R^2$ is selected from the group consisting of alkyl groups or hydroxyalkyl groups;

$R^3$ is selected from the group consisting of cycloalkyl groups having from 4 to 8 carbon atoms, said cycloalkyl groups being optionally substituted by 1 to 3 alkyl groups, 4 to 8-membered heterocyclic groups having 1 to 3 heteroatoms, said heterocyclic groups being optionally substituted by 1 to 3 alkyl groups and the heteroatoms in said heterocyclic groups being selected from the group consisting of O, N, and S, all alkyl and alkoxy groups independently having from 1 to 3 carbon atoms.

Preferably, the organic template of formula (I) is a template of formula (II)

wherein $R^3$ is selected from the group consisting of cycloalkyl groups, said cycloalkyl groups being optionally substituted by 1 to 3 methyl groups, and said cycloalkyl groups having from 4 to 8 carbon atoms, preferably 6 carbon atoms.

In a more preferred embodiment the template of formula (I) or of formula II is selected from the group of templates of formula I or formula II in which $R^3$ is selected from the group consisting of cyclohexyl, methylcyclohexyl, dimethylcyclohexyl, trimethylcyclohexyl, tetramethylcyclohexyl, pentamethylcyclohexyl, cyclopentyl, methylcyclopentyl, dimethylcyclopentyl, trimethylcyclopentyl, tetramethylcyclopentyl, cycloheptyl, methylcycloheptyl, dimethylcycloheptyl, trimethylcycloheptyl, tetramethylcycloheptyl, pentamethylcycloheptyl, hexamethylcycloheptyl, and piperidinyl. Most preferably the template is N,N-dimethylcyclohexylamine.

In a further, less preferred, embodiment the template of formula (I) or of formula (II) may be used in combination with one or more additional templates normally used in the manufacture of silicoaluminophosphates of CHA framework type. These additional templates include: the group of tetraethylammonium compounds, such as tetraethylammonium hydroxide (TEAOH), tetraethylammonium phosphate, tetraethylammonium fluoride, tetraethylammonium bromide, tetraethylammonium chloride and tetraethylammonium acetate and also include DPA, isopropylamine, cyclohexylamine, morpholine, methylbutylamine, diethanolamine, and triethylamine.

Typically, when a template of formula (I) or formula (II), preferably N,N-dimethylcyclohexylamine, is used the resulting silicoaluminophosphates of CHA framework type have a Si per CHA cage ratio within the range of from 0.1 to 1.0, preferably of from 0.15 to 0.8 and more preferably of from 0.2 to 0.7. When tetraethylammonium hydroxide is used as the sole organic templating material, silicoaluminophosphates of CHA framework type having Si per CHA cage values approximating to 1 are normally obtained. Typically, when templates of formula I are used it is possible to achieve Si per CHA cage ratios as low as 0. The preferred template in this context is N,N-dimethylcyclohexylamine, providing Si per CHA cage ratios of less than 0.98.

The sources of aluminum, phosphorus and silicon suitable for use in the synthesis of molecular sieves according to the present invention are typically those known in the art or as described in the literature for the production of the SAPO concerned. The aluminum source may be, for example, an aluminum oxide (alumina), optionally hydrated, an aluminum salt, especially a phosphate, an aluminate, or a mixture thereof. A preferred source is a hydrated alumina, most preferably pseudoboehmite, which contains about 75% $Al_2O_3$ and 25% $H_2O$ by weight. Advantageously, the source of phosphorus is a phosphoric acid, especially orthophosphoric acid, but other sources, for example, organic phosphates, e.g., triethyl phosphate, and aluminophosphates may be used. Advantageously, the source of silicon is silica, for example colloidal silica, fumed silica, or an organic silicon source, e.g., a tetraalkyl orthosilicate, especially tetraethyl orthosilicate. When tetraethylorthosilicate is used as a source of silicon, CHA/AEI intergrowth of very high CHA character is obtained.

The molecular sieve synthesis mixture may also contain a source of fluoride ions. The source of fluoride ions may be any compound capable of releasing fluoride ions in the molecular sieve synthesis mixture. Non-limiting examples of such sources of fluoride ions include salts containing one or several fluoride ions, such as metal fluorides, preferably, sodium fluoride, potassium fluoride, calcium fluoride, magnesium fluoride, strontium fluoride, barium fluoride, ammonium fluoride, tetraalkylammonium fluorides, such as tetramethylammonium fluoride, tetraethylammonium fluoride, hydrogen fluoride, $[(C_2H_5)_4N]PF_6$, $NaHF_2$, $HPF_6NH_4PF_6$, $H_2SiF_6$, $(NH_4)_2SiF_6$, $NH_4HF_2$, $NaPF_6$, $AlF_3$ (anhydrous or hydrate), $(NH_4)_3AlF_6$, $(NH_4)_2TiF_6$, $(NH_4)_2ZrF_6$, $(NH_4)_2GeF_6$, $(NH_4)_2SnF_6$. The fluoride source is preferably selected from $(NH_4)_2SiF_6$, $NH_4HF_2$; $HPF_6$, $H_2SiF_6$, $AlF_3$ (anhydrous or hydrate), $NH_4PF_6$, $NaPF_6$, HF, more preferably $(NH_4)_2SiF_6$, $HPF_6$, $H_2SiF_6$, $AlF_3$ (anhydrous or hydrate), $NH_4PF_6$, HF, and most preferably HF.

Method for Making Molecular Sieve Catalyst Compositions

The silicoaluminophosphate molecular sieves of the present invention may be combined with one or more formulating agents, to form a molecular sieve catalyst composition or a formulated molecular sieve catalyst composition. The formulating agents may be one or more materials selected from the group consisting of binding agents, matrix or filler materials, catalytically active materials and mixtures thereof. This formulated molecular sieve catalyst composition is formed into useful shape and sized particles by well-known techniques such as spray drying, pelletizing, extrusion, and the like.

There are many different binders that are useful in forming the molecular sieve catalyst composition. Non-limiting examples of binders that are useful alone or in combination include various types of hydrated alumina, silicas, and/or other inorganic oxide sol. One preferred alumina containing sol is aluminium chlorhydrol. The inorganic oxide sol acts like glue binding the synthesized molecular sieves and other materials such as the matrix together, particularly after thermal treatment. Upon heating, the inorganic oxide sol, preferably having a low viscosity, is converted into an inorganic oxide matrix component. For example, an alumina sol will convert to an aluminium oxide matrix following heat treatment.

Aluminium chlorhydrol, a hydroxylated aluminium based sol containing a chloride counter ion, has the general formula of $Al_mO_n(OH)_oCl_p\cdot x(H_2O)$ wherein m is 1 to 20, n is 1 to 8, o is 5 to 40, p is 2 to 15, and x is 0 to 30. In one embodiment, the binder is $Al_{13}O_4(OH)_{24}Cl_7\cdot 12(H_2O)$ as is described in G. M. Wolterman, et al., Stud. Surf. Sci. and Catal., 76, pages 105-144 (1993), which is herein incorporated by reference. In another embodiment, one or more binders are combined with one or more other non-limiting examples of alumina materials such as aluminium oxyhydroxide, γ-alumina, boehmite, diaspore, and transitional aluminas such as α-alumina, β-alumina, γ-alumina, δ-alumina, ε-alumina, κ-alumina, and ρ-alumina, aluminium trihydroxide, such as gibbsite, bayerite, nordstrandite, doyelite, and mixtures thereof.

In another embodiment, the binders are alumina sols, predominantly comprising aluminium oxide, optionally including some silicon. In yet another embodiment, the binders are peptised alumina made by treating alumina hydrates such as pseudobohemite, with an acid, preferably an acid that does not contain a halogen, to prepare sols or aluminium ion solutions.

The molecular sieve may be combined with one or more matrix material(s). Matrix materials are typically effective in reducing overall catalyst cost, act as thermal sinks assisting in shielding heat from the catalyst composition for example during regeneration, densifying the catalyst composition, increasing catalyst strength such as crush strength and attrition resistance, and to control the rate of conversion in a particular process.

Non-limiting examples of matrix materials include one or more of the following: rare earth metals, metal oxides including titania, zirconia, magnesia, thoria, beryllia, quartz, silica or sols, and mixtures thereof, for example silica-magnesia, silica-zirconia, silica-titania, silica-alumina and silica-alumina-thoria. In one embodiment, matrix materials are natural clays such as those from the families of montmorillonite and kaolin. These natural clays include sabbentonites and those kaolins known as, for example, Dixie, McNamee, Georgia and Florida clays. Non-limiting examples of other matrix materials include: haloysite, kaolinite, dickite, nacrite, or anauxite. In one embodiment, the matrix material, preferably any of the clays, are subjected to well known modification processes such as calcination and/or acid treatment and/or chemical treatment.

Upon combining the molecular sieve and the matrix material, optionally with a binder, in a liquid to form a slurry, mixing, preferably rigorous mixing is needed to produce a substantially homogeneous mixture containing the molecular sieve. Non-limiting examples of suitable liquids include one or a combination of water, alcohol, ketones, aldehydes, and/or esters. The most preferred liquid is water. In one embodiment, the slurry is colloid-milled for a period of time sufficient to produce the desired slurry texture, sub-particle size, and/or sub-particle size distribution.

The molecular sieve and matrix material, and the optional binder, may be in the same or different liquid, and may be combined in any order, together, simultaneously, sequentially, or a combination thereof. In the preferred embodiment, the same liquid, preferably water is used.

In one embodiment, the slurry of the molecular sieve, binder and matrix materials is mixed or milled to achieve a sufficiently uniform slurry of sub-particles of the molecular sieve catalyst composition that is then fed to a forming unit that produces the molecular sieve catalyst composition. In a preferred embodiment, the forming unit is spray dryer. Typically, the forming unit is maintained at a temperature sufficient to remove most of the liquid from the slurry, and from the resulting molecular sieve catalyst composition. The resulting catalyst composition when formed in this way takes the form of microspheres.

In another embodiment, the formulated molecular sieve catalyst composition contains from about 1% to about 99%, more preferably from about 5% to about 90%, and most preferably from about 10% to about 80%, by weight of the molecular sieve based on the total weight of the molecular sieve catalyst composition.

In another embodiment, the weight percent of binder in or on the spray dried molecular sieve catalyst composition based on the total weight of the binder, molecular sieve, and matrix material is from about 2% by weight to about 30% by weight, preferably from about 5% by weight to about 20% by weight, and more preferably from about 7% by weight to about 15% by weight.

Once the molecular sieve catalyst composition is formed in a substantially dry or dried state, to further harden and/or activate the formed catalyst composition, a heat treatment such as calcination, at an elevated temperature is usually performed. A conventional calcination environment is air that typically includes a small amount of water vapour. Typical calcination temperatures are in the range from about 400° C. to about 1,000° C., preferably from about 500° C. to about 800° C., and most preferably from about 550° C. to about 700° C., preferably in a calcination environment such as air, nitrogen, helium, flue gas (combustion product lean in oxygen), or any combination thereof In one embodiment, calcination of the formulated molecular sieve catalyst composition is carried out in any number of well known devices including rotary calciners, fluid bed calciners, batch ovens, and the like. Calcination time is typically dependent on the degree of hardening of the molecular sieve catalyst composition and the temperature.

In addition to the molecular sieve of the present invention, the catalyst compositions of the present invention may comprise one or several other catalytically active materials, such as silicoaluminophosphates or aluminophosphates having a different framework type than the molecular sieves of the present invention or zeolites (aluminosilicates) of any framework type. In another embodiment, the molecular sieve of the present invention may be bound to another molecular sieve, as disclosed for example in the following: SAPO-34 bound AlPO$_4$-5 (U.S. Pat. No. 5,972,203), PCT WO 98/57743 published Dec. 23, 1988 (molecular sieve and Fischer-Tropsch), U.S. Pat. No. 6,300,535 (MFI-bound zeolites), and mesoporous molecular sieves (U.S. Pat. Nos. 6,284,696, 5,098,684, 5,102,643 and 5,108,725), which are all herein fully incorporated by reference. Binder may no longer be necessary in such systems.

In a further embodiment, the molecular sieve of the present invention may be combined with a metal catalyst, for example as a Fischer-Tropsch catalyst.

Process for Using the Molecular Sieve Catalyst Compositions

The molecular sieve catalysts and compositions of the present invention are useful in a variety of processes including: cracking, hydrocracking, isomerization, polymerisation, reforming, hydrogenation, dehydrogenation, dewaxing, hydrodewaxing, absorption, alkylation, transalkylation, dealkylation, hydrodecylization, disproportionation, oligomerization, dehydrocyclization and combinations thereof.

The preferred processes of the present invention include a process directed to the conversion of a feedstock comprising one or more oxygenates to one or more olefin(s) and a process directed to the conversion of ammonia and one or more oxygenates to alkyl amines and in particular methylamines.

In a preferred embodiment of the process of the invention, the feedstock contains one or more oxygenates, more specifically, one or more organic compound(s) containing at least one oxygen atom. In the most preferred embodiment of the process of invention, the oxygenate in the feedstock is one or more alcohol(s), preferably aliphatic alcohol(s) where the aliphatic moiety of the alcohol(s) has from 1 to 20 carbon atoms, preferably from 1 to 10 carbon atoms, and most preferably from 1 to 4 carbon atoms. The alcohols useful as feedstock in the process of the invention include lower straight and branched chain aliphatic alcohols and their unsaturated counterparts.

Non-limiting examples of oxygenates include methanol, ethanol, n-propanol, isopropanol, methyl ethyl ether, dimethyl ether, diethyl ether, di-isopropyl ether, formaldehyde, dimethyl carbonate, dimethyl ketone, acetic acid, and mixtures thereof.

The most preferred process is generally referred to as gas-to-olefins (GTO) or alternatively, methanol-to-olefins (MTO). In a MTO process, typically an oxygenated feedstock, most preferably a methanol containing feedstock, is converted in the presence of a molecular sieve catalyst composition into one or more olefin(s), preferably and predominantly, ethylene and/or propylene, often referred to as light olefin(s).

The feedstock, in one embodiment, contains one or more diluent(s), typically used to reduce the concentration of the feedstock, and generally non-reactive to the feedstock or molecular sieve catalyst composition. Non-limiting examples of diluents include helium, argon, nitrogen, carbon monoxide, carbon dioxide, water, essentially non-reactive paraffins (especially alkanes such as methane, ethane, and propane), essentially non-reactive aromatic compounds, and mixtures thereof. The most preferred diluents are water and nitrogen, with water being particularly preferred.

The process for converting a feedstock, especially a feedstock containing one or more oxygenates, in the presence of a molecular sieve catalyst composition of the invention, is carried out in a reaction process in a reactor, where the process is a fixed bed process, a fluidised bed process (includes a turbulent bed process), preferably a continuous fluidised bed process, and most preferably a continuous high velocity fluidised bed process.

The reaction processes can take place in a variety of catalytic reactors such as hybrid reactors that have a dense bed or fixed bed reaction zones and/or fast fluidised bed reaction zones coupled together, circulating fluidised bed reactors, riser reactors, and the like. Suitable conventional reactor types are described in for example U.S. Pat. No. 4,076,796, U.S. Pat. No. 6,287,522 (dual riser), and *Fluidization Engineering*, D. Kunii and O. Levenspiel, Robert E. Krieger Publishing Company, New York, N.Y. 1977, which are all herein fully incorporated by reference.

The preferred reactor type are riser reactors generally described in *Riser Reactor, Fluidization and Fluid-Particle Systems*, pages 48 to 59, F. A. Zenz and D. F. Othmo, Reinhold Publishing Corporation, New York, 1960, and U.S. Pat. No. 6,166,282 (fast-fluidised bed reactor), and U.S. patent application Ser. No. 09/564,613 filed May 4, 2000 (multiple riser reactor), which are all herein fully incorporated by reference.

In the preferred embodiment, a fluidised bed process or high velocity fluidised bed process includes a reactor system, a regeneration system and a recovery system.

The reactor system preferably is a fluid bed reactor system having a first reaction zone within one or more riser reactor(s) and a second reaction zone within at least one disengaging vessel, preferably comprising one or more cyclones. In one embodiment, the one or more riser reactor(s) and disengaging vessel is contained within a single reactor vessel. Fresh feedstock, preferably containing one or more oxygenates, optionally with one or more diluent(s), is fed to the one or more riser reactor(s) in which a molecular sieve catalyst composition or coked version thereof is introduced. In one embodiment, the molecular sieve catalyst composition or coked version thereof is contacted with a liquid or gas, or combination thereof, prior to being introduced to the riser reactor(s), preferably the liquid is water or methanol, and the gas is an inert gas such as nitrogen.

The feedstock entering the reactor system is preferably converted, partially or fully, in the first reaction zone into a gaseous effluent that enters the disengaging vessel along with a coked molecular sieve catalyst composition. In the preferred embodiment, cyclone(s) within the disengaging vessel are designed to separate the molecular sieve catalyst composition, preferably a coked molecular sieve catalyst composition, from the gaseous effluent containing one or more olefin(s) within the disengaging zone. Cyclones are preferred, however, gravity effects within the disengaging vessel will also separate the catalyst compositions from the gaseous effluent. Other methods for separating the catalyst compositions from the gaseous effluent include the use of plates, caps, elbows, and the like.

In one embodiment of the disengaging system, the disengaging system includes a disengaging vessel; typically a lower portion of the disengaging vessel is a stripping zone. In the stripping zone the coked molecular sieve catalyst composition is contacted with a gas, preferably one or a combination of steam, methane, carbon dioxide, carbon monoxide, hydrogen, or an inert gas such as argon, preferably steam, to recover adsorbed hydrocarbons from the coked molecular sieve catalyst composition that is then introduced to the regeneration system. In another embodiment, the stripping zone is in a separate vessel from the disengaging vessel and the gas is passed at a gas hourly superficial velocity (GHSV) of from 1 $hr^{-1}$ to about 20,000 $hr^{-1}$ based on the volume of gas to volume of coked molecular sieve catalyst composition, preferably at an elevated temperature from 250° C. to about 750° C., preferably from about 350° C. to 650° C., over the coked molecular sieve catalyst composition.

The conversion temperature employed in the conversion process, specifically within the reactor system, is in the range of from about 200° C. to about 1000° C., preferably from about 250° C. to about 800° C., more preferably from about 250° C. to about 750° C., yet more preferably from about 300° C. to about 650° C., yet even more preferably from about 350° C. to about 600° C. most preferably from about 350° C. to about 550° C.

The conversion pressure employed in the conversion process, specifically within the reactor system, varies over a wide range including autogenous pressure. The conversion pressure is based on the partial pressure of the feedstock exclusive of any diluent therein. Typically the conversion pressure employed in the process is in the range of from about 0.1 kPaa to about 5 MPaa, preferably from about 5 kPaa to about 1 MPaa, and most preferably from about 20 kPaa to about 500 kpaa.

The weight hourly space velocity (WHSV), particularly in a process for converting a feedstock containing one or more oxygenates in the presence of a molecular sieve catalyst composition within a reaction zone, is defined as the total weight of the feedstock excluding any diluents to the reaction zone per hour per weight of molecular sieve in the molecular sieve catalyst composition in the reaction zone. The WHSV is maintained at a level sufficient to keep the catalyst composition in a fluidised state within a reactor. Typically, the WHSV ranges from about 1 $hr^{-1}$ to about 5000 $hr^{-1}$, preferably from about 2 $hr^{-1}$ to about 3000 $hr^{-1}$, more preferably from about 5 $hr^{-1}$ to about 1500 $hr^{-1}$, and most preferably from about 10 $hr^{-1}$ to about 1000 $hr^{-1}$. In one preferred embodiment, the WHSV is greater than 20 $hr^{-}$; preferably the WHSV for conversion of a feedstock containing methanol and dimethyl ether is in the range of from about 20 $hr^{-1}$ to about 300 $hr^{-1}$.

The superficial gas velocity (SGV) of the feedstock including diluent and reaction products within the reactor system is preferably sufficient to fluidise the molecular sieve catalyst composition within a reaction zone in the reactor. The SGV in the process, particularly within the reactor system, more particularly within the riser reactor(s), is at least 0.1 meter per second (m/s), preferably greater than 0.5 m/s, more preferably greater than 1 m/sec, even more preferably greater than 2 m/s, yet even more preferably greater than 3 m/sec, and most preferably greater than 4 m/s. See for example U.S. patent application Ser. No. 09/708,753 filed Nov. 8, 2000, which is herein incorporated by reference.

In one preferred embodiment of the process for converting an oxygenate to olefin(s) using a silicoaluminophosphate molecular sieve catalyst composition, the process is operated at a WHSV of at least 20 $hr^{-1}$ and a Temperature Corrected Normalized Methane Selectivity (TCNMS) of less than 0.016, preferably less than or equal to 0.01. See for example U.S. Pat. No. 5,952,538, which is herein fully incorporated by reference.

The coked molecular sieve catalyst composition is withdrawn from the disengaging vessel, preferably by one or more cyclones(s), and introduced to the regeneration system. The regeneration system comprises a regenerator where the coked catalyst composition is contacted with a regeneration medium, preferably a gas containing oxygen, under general regeneration conditions of temperature, pressure and residence time.

Non-limiting examples of the regeneration medium include one or more of oxygen, $O_3$, $SO_3$, $N_2O$, NO, $NO_2$, $N_2O_5$, air, air diluted with nitrogen or carbon dioxide, oxygen and water (U.S. Pat. No. 6,245,703), carbon monoxide and/or hydrogen. The regeneration conditions are those capable of burning coke from the coked catalyst composition, preferably to a level less than 0.5 weight percent based on the total weight of the coked molecular sieve catalyst composition entering the regeneration system. The coked molecular sieve catalyst composition withdrawn from the regenerator forms a regenerated molecular sieve catalyst composition.

The regeneration temperature is in the range of from about 200° C. to about 1500° C., preferably from about 300° C. to about 1000° C., more preferably from about 450° C. to about 750° C., and most preferably from about 550° C. to 700° C. The regeneration pressure is in the range of from about 15 psia (103 kPaa) to about 500 psia (3448 kpaa), preferably from about 20 psia (138 kpaa) to about 250 psia (1724 kpaa), more preferably from about 25 psia (172 kPaa) to about 150 psia (1034 kPaa), and most preferably from about 30 psia (207 kPaa) to about 60 psia (414 kpaa).

The preferred residence time of the molecular sieve catalyst composition in the regenerator is in the range of from about one minute to several hours, most preferably about one minute to 100 minutes, and the preferred volume of oxygen in the gas is in the range of from about 0.01 mole percent to about 5 mole percent based on the total volume of the gas.

In one embodiment, regeneration promoters, typically metal containing compounds such as platinum, palladium and the like, are added to the regenerator directly, or indirectly, for example with the coked catalyst composition. Also, in another embodiment, a fresh molecular sieve catalyst composition is added to the regenerator containing a regeneration medium of oxygen and water as described in U.S. Pat. No. 6,245,703, which is herein fully incorporated by reference.

In an embodiment, a portion of the coked molecular sieve catalyst composition from the regenerator is returned directly to the one or more riser reactor(s), or indirectly, by pre-contacting with the feedstock, or contacting with fresh molecular sieve catalyst composition, or contacting with a regenerated molecular sieve catalyst composition or a cooled regenerated molecular sieve catalyst composition.

Coke levels on the molecular sieve catalyst composition are measured by withdrawing from the conversion process the molecular sieve catalyst composition at a point in the process and determining its carbon content. Typical levels of coke on the molecular sieve catalyst composition, after regeneration is in the range of from 0.01 weight percent to about 15 weight percent, preferably from about 0.1 weight percent to about 10 weight percent, more preferably from about 0.2 weight percent to about 5 weight percent, and most preferably from about 0.3 weight percent to about 2 weight percent based on the total weight of the molecular sieve and not the total weight of the molecular sieve catalyst composition.

In one preferred embodiment, the mixture of fresh molecular sieve catalyst composition and regenerated molecular sieve catalyst composition and/or cooled regenerated molecular sieve catalyst composition contains in the range of from about 1 to 50 weight percent, preferably from about 2 to 30 weight percent, more preferably from about 2 to about 20 weight percent, and most preferably from about 2 to about 10 coke or carbonaceous deposit based on the total weight of the mixture of molecular sieve catalyst compositions. See for example U.S. Pat. No. 6,023,005, which is herein fully incorporated by reference.

The gaseous effluent is withdrawn from the disengaging system and is passed through a recovery system. There are many well-known recovery systems, techniques and sequences that are useful in separating olefin(s) and purifying olefin(s) from the gaseous effluent. Recovery systems generally comprise one or more or a combination of a various separation, fractionation and/or distillation towers, columns, splitters, or trains, reaction systems such as ethylbenzene manufacture (U.S. Pat. No. 5,476,978) and other derivative processes such as aldehydes, ketones and ester manufacture (U.S. Pat. No. 5,675,041), and other associated equipment for example various condensers, heat exchangers, refrigeration systems or chill trains, compressors, knock-out drums or pots, pumps, and the like.

The molecular sieve materials and catalyst compositions of the present invention may be used in the manufacture of alkylamines, using ammonia. Examples of suitable processes are as described in published European Patent Application EP 0 993 867 A1, and in U.S. Pat. No. 6,153,798 to Hidaka et al., which are herein fully incorporated by reference.

In order to provide a better understanding of the present invention including representative advantages thereof, the following examples are offered.

EXAMPLES

XRD

X-ray Powder Diffractograms were recorded on Siemens D500 diffractometer with voltage of 40 kV and current of 30 mA, using a Cu target and Ni-filter ($\lambda$=0.154 nm). Elemental analysis of Al, Si, and P was performed using the Inductively Coupled Plasma (ICP) spectroscopy.

Example 1

Eight samples were prepared and characterized by the procedures described below.

The following ingredients were mixed, in sequence, and blended into a uniform gel using a microhomogenizer (Tissue Tearor Model 98730 available from Biospec Products, Inc, USA): 85 wt % $H_3PO_4$ (obtained from Aldrich Chemical Company), H$_2$O, Cabosil™ (available from Cabot Corporation, Illinois, USA), Catapal™ A (74 wt % Al$_2$O$_3$, available from CONDEA Vista Company, Texas, USA), and then N,N-dimethylcyclohexylamine (DMCHA; (CH$_3$)$_2$NC$_6$H$_{11}$; obtained from Aldrich Chemical Company, USA). The molar ratio of the ingredients was as follows:

2.0 DMCHA:1.0 Al$_2$O$_3$:x SiO$_2$:1.0 P$_2$O$_5$:40 H$_2$O
x=0,0.1,0.2 and 0.3

In the case where x=0.1, 14.58 g deionized water was first added to 5.65 g H$_3$PO$_4$. Then 3.38 g Catapal™ A, 0.16 g Cabosil™ and 6.23 g N,N-dimethylcyclohexylamine were sequentially and slowly added with stirring to form a gel. The gel was treated with the microhomogenizer to make a uniform gel. The pH of the gel was 5 as measured with pH paper. This gel was divided into two equal portions and each was sealed in Teflon lined autoclaves. The autoclaves were placed in an oven whose temperature was set at 180° C. The autoclaves were taken out of the oven after 3 and 7 days, respectively. After cooling, the pH of the supernatant was measured to be 9.

The solid products in the autoclaves were centrifuged and washed several times with deionized water, until the conductivity of the washing fluid was below 50 S/cm, and were then dried in a 60° C. vacuum oven overnight. This procedure was repeated for the molecular sieve preparation mixtures for which x=0, x=0.2 and x=0.3, respectively, by adapting the amount of silicon source used.

Figure 1:
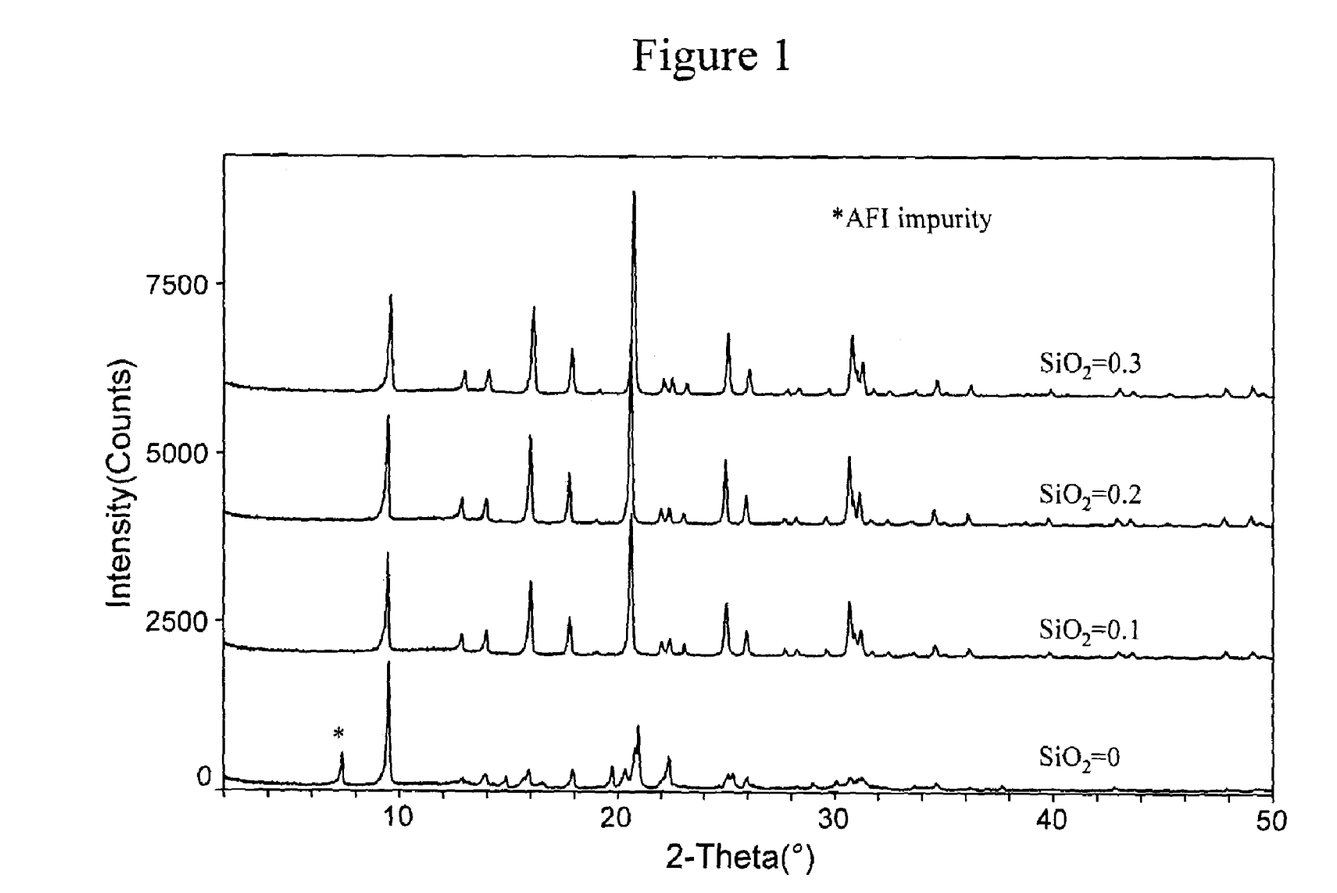
FIG. 1 shows the XRD patterns of crystalline molecular sieves of CHA framework type comprising N,N-dimethylcyclohexylamine within their intra-crystalline structures obtained after 3 days of crystallization, using varying amounts of silicon source in the molecular sieve synthesis mixture.

X-ray powder diffraction patterns of the products obtained from molecular sieve synthesis mixtures for which x=0, 0.1, 0.2 and 0.3, respectively, obtained after three days of crystallization are shown in FIG. 1. Table Ib gives the list of XRD peaks for the product obtained after 3 days of crystallization from a molecular sieve synthesis mixture for which x=0.1.

TABLE Ib

| 2 θ | d (A) | I % |
|---|---|---|
| 9.46 | 9.34 | 63 |
| 12.86 | 6.88 | 12 |
| 13.98 | 6.33 | 16 |
| 16.02 | 5.53 | 51 |
| 17.80 | 4.98 | 24 |
| 19.06 | 4.65 | 2 |
| 20.62 | 4.30 | 100 |
| 22.06 | 4.03 | 8 |
| 22.42 | 3.96 | 11 |
| 23.10 | 3.85 | 7 |
| 25.02 | 3.56 | 36 |
| 25.96 | 3.43 | 16 |
| 27.72 | 3.22 | 4 |
| 28.26 | 3.16 | 4 |
| 29.62 | 3.01 | 4 |
| 30.68 | 2.91 | 37 |
| 31.18 | 2.87 | 18 |
| 31.68 | 2.82 | 2 |
| 32.44 | 2.76 | 2 |
| 33.62 | 2.66 | 3 |
| 34.60 | 2.59 | 8 |
| 35.02 | 2.56 | 1 |
| 36.18 | 2.48 | 5 |
| 38.76 | 2.32 | 1 |
| 39.84 | 2.26 | 3 |
| 42.98 | 2.10 | 3 |
| 43.58 | 2.08 | 3 |
| 45.28 | 2.00 | 1 |
| 46.92 | 1.93 | 1 |
| 47.84 | 1.90 | 4 |
| 49.02 | 1.86 | 4 |
| 49.52 | 1.84 | 1 |

The XRD patterns in FIG. 1 show that the products obtained after 3 days of crystallization from mixtures in which x=0.1, 0.2 or 0.3 are pure silicoaluminophosphates of the CHA framework type. The product obtained after 3 days of crystallization from the mixture in which x=0.0 appeared to be a mixture of ALPO-5 and an aluminophosphate having the CHA framework type.

Figure 2:
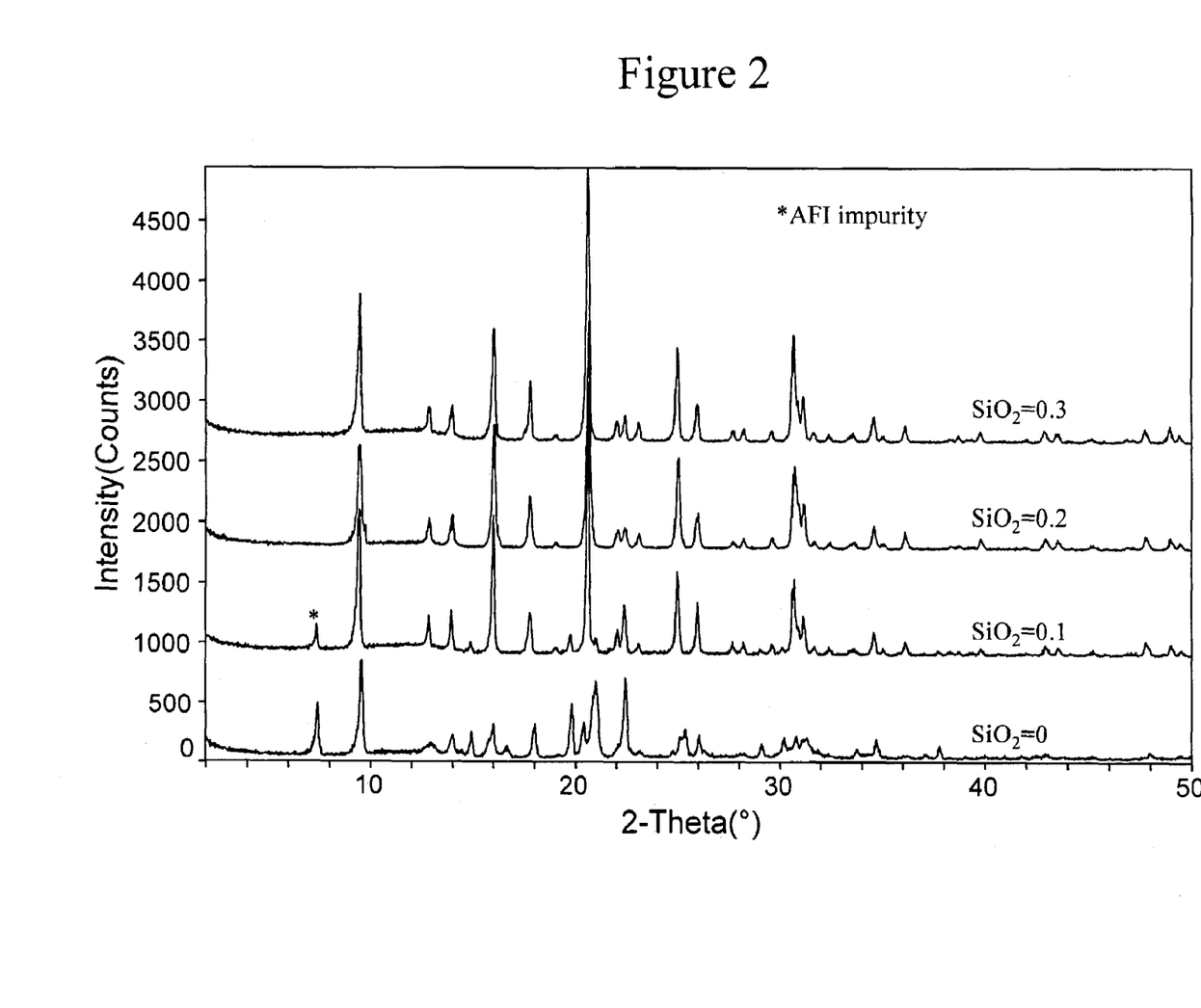
FIG. 2 shows the XRD patterns of crystalline molecular sieves of CHA framework type comprising N,N-dimethylcyclohexylamine within their intra-crystalline structures obtained after 7 days of crystallization, using varying amounts of silicon source in the molecular sieve synthesis mixture.

X-ray powder diffraction patterns of the products for x=0, 0.1, 0.2 and 0.3 obtained after seven days of crystallization are shown in FIG. 2. The XRD patterns in FIG. 2 show that, after seven days of crystallization, small amounts of a crystalline impurity having the AFI framework type were formed from the molecular sieve preparation mixture for which x=0.1. The molecular sieve preparation mixtures for which x=0.2 or 0.3 gave pure silicoaluminophosphate molecular sieves having the CHA framework type. The product yields (expressed as the weight percent of the final product versus the weight of the starting gel) along with the chemical compositions of the products as determined by elemental analysis, are given in Table II.

The results shown in FIG. 1, FIG. 2, Table Ib and Table II show that pure silicoaluminophosphates with low Si contents can be made in good yields from a molecular sieve preparation mixture containing N,N-dimethylcyclohexylamine as organic template. The results also show that ALPOs, although somewhat impure, could also be made with this template.

TABLE II

| Crystallization | Molecular sieve preparation mixture composition | | | |
|---|---|---|---|---|
| Time (days) | | x = 0 | x = 0.1 | x = 0.2 | x = 0.3 |
| 3 | Yield | 13.2* | 14.1 | 17.0 | 18.6 |
| 3 | Product composition | — | AlSi$_{0.07}$P$_{0.943}$ | AlSi$_{0.119}$P$_{0.881}$ | AlSi$_{0.154}$P$_{0.866}$ |
| 3 | Si/CHA cage | — | 0.42 | 0.714 | 0.924 |
| 7 | Yield | 15.0* | 16.1* | 17.1 | 19.3 |

*Impure

Example 2

Four samples were prepared and characterized by the procedures described below.

The following ingredients were mixed, in sequence, and blended into a uniform gel using a microhomogenizer (Tissue Tearor Model 98730 available from Biospec Products, Inc, USA): 85 wt % H$_3$PO$_4$ (obtained from Aldrich Chemical Company), H$_2$O, Cabosil™ (available from Cabot Corporation, Illinois, USA), Catapal™ A (74 wt % Al$_2$O$_3$, available from CONDEA Vista Company, Texas, USA), and then N,N-dimethylcyclohexylamine (DMCHA) (obtained from Aldrich Chemical Company, USA). Finally, HF (50% aqueous solution from Aldrich Chemical Company, USA) was added to the synthesis gel as the last ingredient. The molar ratio of the ingredients was as follows:

0.5 HF:2.0 *DMCHA*:1.0 Al$_2$O$_3$:*x* SiO$_2$:1.0 P$_2$O$_5$:40 H$_2$O

*x* = 0, 0.1, 0.2 and 0.3

The procedure of example 1 was followed, with a crystallization temperature of 180° C. and a crystallization time of 3 days.

Figure 3:
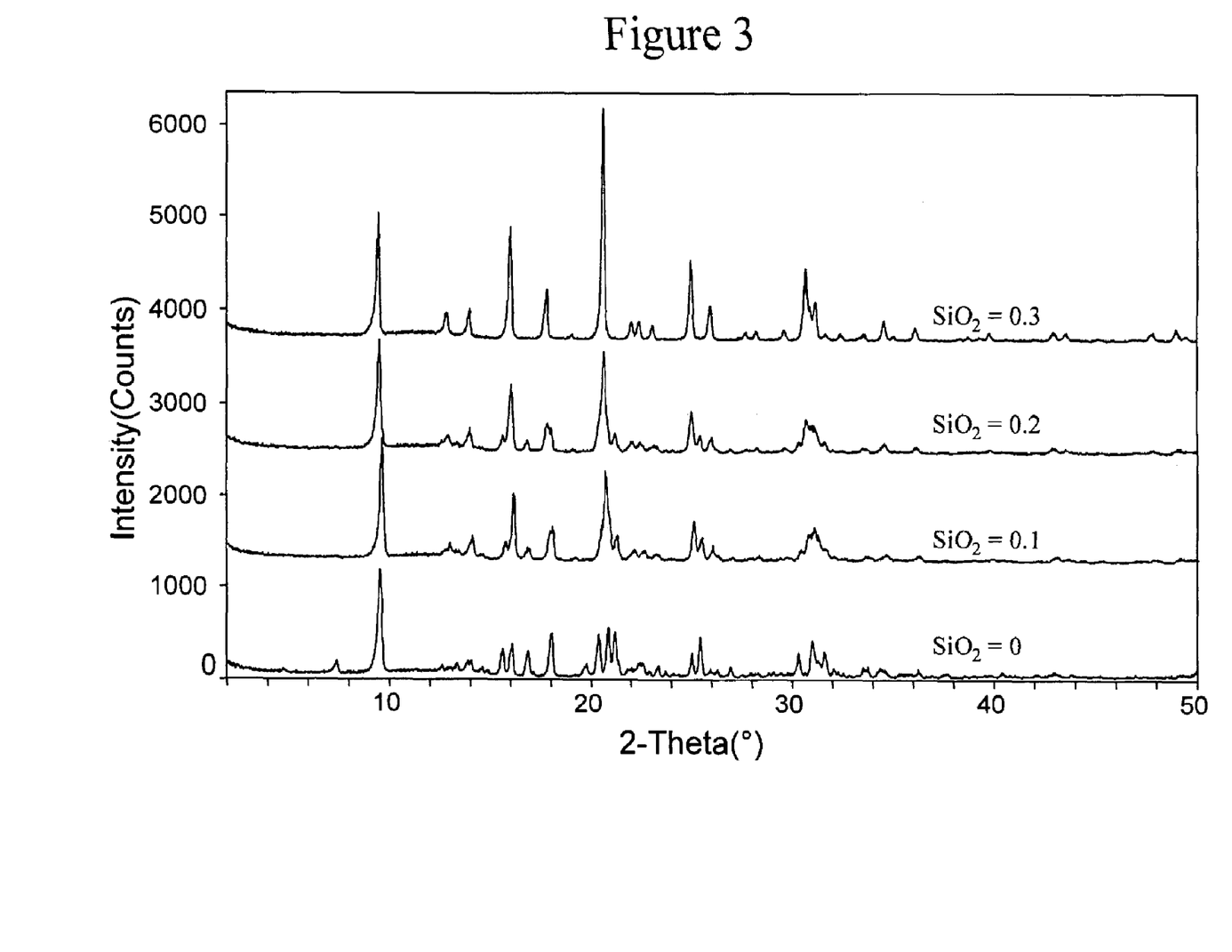
FIG. 3 shows the XRD patterns of crystalline molecular sieves of CHA framework type comprising N,N-dimethylcyclohexylamine within their intra-crystalline structures obtained after 3 days of crystallization, using HF as well as varying amounts of silicon source in the molecular sieve synthesis mixture.

X-ray powder diffraction patterns of the products obtained from molecular sieve synthesis mixtures for which x=0, 0.1, 0.2 and 0.3, respectively, obtained after three days of crystallization are shown in FIG. 3. Table IIIb gives the list of XRD peaks for the product obtained after 3 days of crystallization from a molecular sieve synthesis mixture for which x=0.1.

TABLE IIIb

| 2 θ | d (A) | I % |
|---|---|---|
| 9.54 | 9.26 | 100 |
| 12.92 | 6.85 | 9 |
| 13.36 | 6.62 | 4 |
| 14.04 | 6.30 | 20 |
| 14.56 | 6.08 | 3 |
| 15.68 | 5.65 | 15 |
| 16.08 | 5.51 | 57 |
| 16.80 | 5.27 | 8 |
| 17.88 | 4.96 | 25 |
| 18.00 | 4.92 | 27 |
| 20.68 | 4.29 | 76 |
| 21.22 | 4.18 | 21 |
| 22.12 | 4.02 | 7 |
| 22.60 | 3.93 | 8 |
| 23.18 | 3.83 | 4 |
| 25.04 | 3.55 | 32 |
| 25.44 | 3.50 | 20 |
| 26.00 | 3.42 | 10 |
| 26.26 | 3.39 | 3 |
| 27.00 | 3.30 | 3 |
| 28.28 | 3.15 | 4 |
| 30.36 | 2.94 | 9 |
| 30.74 | 2.91 | 22 |
| 31.04 | 2.88 | 26 |
| 31.18 | 2.87 | 19 |
| 31.60 | 2.83 | 9 |
| 33.64 | 2.66 | 3 |
| 34.60 | 2.59 | 5 |
| 36.24 | 2.48 | 5 |
| 43.02 | 2.10 | 4 |

The XRD patterns in FIG. 3 show that the products obtained after 3 days of crystallization from mixtures in which x=0.1, 0.2 or 0.3 are pure silicoaluminophosphates of the CHA framework type. The product obtained after 3 days of crystallization from the mixture in which x=0.0 appeared to be a mixture of AlPO4-5 and an aluminophosphate having the CHA framework type. It is apparent that the presence of fluoride causes some minor distortion to the crystal structure, resulting in more and broader diffraction peaks. The higher the SiO$_2$ amount, the less the distortion.

The product yields (expressed as the weight percent of the final product versus the weight of the starting gel) along with the chemical compositions of the products as determined by elemental analysis, are given in Table IV.

TABLE IV

| Yield | Molecular sieve preparation mixture composition | | | |
|---|---|---|---|---|
| Product Comp. | x = 0 | x = 0.1 | x = 0.2 | x = 0.3 |
| Yield | 15.7* | 15.7 | 18.9 | 17.9 |
| F/Al in product | 0.1136 | 0.0872 | 0.0805 | 0.0500 |
| Si/Al in product | 0 | 0.059 | 0.077 | 0.132 |
| Si/CHA cage | 0 | 0.354 | 0.462 | 0.792 |

Persons of ordinary skill in the art will recognize that many modifications may be made to the present invention without departing from the spirit and scope of the present invention. The embodiment described herein is meant to be illustrative only and should not be taken as limiting the invention.

The invention claimed is:

1. A process for preparing low acidity crystalline silicoaluminophosphate molecular sieve of CHA framework type, the process comprising:
  (a) providing a synthesis mixture comprising a source of aluminum, a source of phosphorus, a source of silicon and at least one organic template of formula (I)

$$R^1R^2N\text{—}R^3 \qquad (I)$$

wherein
    $R^1$ and $R^2$ are independently selected from the group consisting of alkyl groups having from 1 to 3 carbon atoms and hydroxyalkyl groups having from 1 to 3 carbon atoms; and
    $R^3$ is selected from the group consisting of 4- to 8-membered cycloalkyl groups, optionally substituted by 1 to 3 alkyl groups having from 1 to 3 carbon atoms; and 4- to 8-membered heterocyclic groups having from 1 to 3 heteroatoms, said heterocyclic groups being optionally substituted by 1 to 3 alkyl groups having from 1 to 3 carbon atoms and the heteroatoms in said heterocyclic groups being selected from the group consisting of O, N, and S; and
  (b) inducing crystallization of crystalline silicoaluminophosphate molecular sieve which is 90% or greater of CHA framework type from the synthesis mixture, wherein the Si/Al ratio in said molecular sieve after calcination is less than 0.167.

2. The process of claim 1, wherein the organic template of formula (I) is a template of formula (II)

$$(CH_3)_2N\text{—}R^3 \qquad (II)$$

wherein R3 is a 4- to 8-membered cycloalkyl group, optionally substituted by 1 to 3 methyl groups.

3. The process of claim 2, wherein $R^3$ is a cyclohexyl group, optionally substituted by 1 to 3 methyl groups.

4. The process of claim 1, wherein the organic template is selected from the group consisting of N,N-dimethyl-cyclohexylamine, N,N-dimethyl-cyclopentylamine, N,N-dimethyl-methylcyclohexylamine, and N,N-dimethyl-methylcyclohexylamine.

5. The process of claim 4, wherein the organic template is N,N-dimethyl-cyclohexylamine.

6. The process of claim 1, wherein the synthesis mixture further comprises at least one source of fluoride ions.

7. The process of claim 6, wherein the source of fluoride ions is hydrogen fluoride.

8. The process of claim 1, wherein an organic template containing tetraethylammonium cations is used in combination with the organic template of formula (I).

9. The process of claim 8, wherein the organic template containing tetraethylammonium cations is selected from the group consisting of tetraethylammonium chloride, tetraethylammonium bromide, tetraethylammonium fluoride and mixtures thereof.

10. The process of claim 1, wherein the molar ratio of template to aluminum in the synthesis mixture, when expressed as the molar ratio of template to alumina (Al$_2$O$_3$), is within the range of from 1.0:1.0 to 3.0:1.0.

11. The process of claim 1, wherein the molar ratio of template to aluminum in the synthesis mixture, when expressed as the molar ratio of template to alumina (Al$_2$O$_3$), is within the range of from 1.5:1.0 to 3.0:1.0.

12. The process of claim 1, further comprising the steps of recovering and calcining the crystalline molecular sieve of CHA framework type to provide an activated silicoaluminophosphate of CHA framework type.

13. A silicoaluminophosphate molecular sieve, 90% or greater of CHA framework type, comprising within its intra-crystalline structure at least one organic template of formula (I)

$$R^1R^2N\text{—}R^3 \quad (I)$$

wherein
- $R^1$ and $R^2$ are independently selected from the group consisting of alkyl groups having from 1 to 3 carbon atoms and hydroxyalkyl groups having from 1 to 3 carbon atoms; and
- $R^3$ is selected from the group consisting of 4- to 8-membered cycloalkyl groups, optionally substituted by 1 to 3 alkyl groups having from 1 to 3 carbon atoms; and 4- to 8-membered heterocyclic groups having from 1 to 3 heteroatoms, said heterocyclic groups being optionally substituted by 1 to 3 alkyl groups having from 1 to 3 carbon atoms and the heteroatoms in said heterocyclic groups being selected from the group consisting of O, N, and S, wherein said silicoaluminophosphate molecular sieve, after removal of the template by calcination, has a Si/Al ratio of less than 0.167.

14. A silicoaluminophosphate molecular sieve, 90% or greater of CHA framework type, comprising within its intra-crystalline structure at least one organic template of formula (II)

$$(CH_3)_2N\text{—}R^3 \quad (II)$$

wherein $R^3$ is a 4- to 8-membered cycloalkyl group, optionally substituted by 1 to 3 methyl groups, and
wherein said silicoaluminophosphate molecular sieve, after removal of the template by calcination, has a Si/Al ratio of less than 0.167.

15. A silicoaluminophosphate molecular sieve according to claim 14, 90% or greater of CHA framework type, comprising N,N-dimethyl-cyclohexylamine within its intra-crystalline structure.

16. The silicoaluminophosphate molecular sieve of claim 15, further comprising fluoride.

17. A crystalline silicoaluminophosphate molecular sieve having a characteristic X-ray powder diffraction pattern containing at least the d-spacings as set forth in Table Ia, wherein the Si/Al ratio in said molecular sieve after calcination is less than 0.167.

18. A crystalline silicoaluminophosphate molecular sieve, having a characteristic X-ray powder diffraction pattern containing at least the d-spacings as set forth in Table Ib, wherein the Si/Al ratio in said molecular sieve after calcination is less than 0.167.

19. The molecular sieve as claimed in claim 17 comprising N,N-dimethylcyclohexylamine within its intra-crystalline structure.

20. A crystalline silicoaluminophosphate molecular sieve having a characteristic X-ray powder diffraction pattern containing at least the d-spacings as set forth in Table IIIa, wherein the Si/Al ratio in said molecular sieve after calcination is less than 0.167.

21. A crystalline silicoaluminophosphate molecular sieve having a characteristic X-ray powder diffraction pattern containing at least the d-spacings as set forth in Table IIIb, wherein the Si/Aratio in said molecular sieve after calcination is less than 0.167.

22. The molecular sieve as claimed in claim 20 comprising N,N-dimethylcyclohexylamine within its intra-crystalline structure and fluoride.

23. A process for forming a molecular sieve catalyst composition, the process comprising combining at least one molecular sieve as claimed in claim 13 with at least one formulating agent.

24. A formulated molecular sieve catalyst composition comprising at least one silicoaluminophosphate molecular sieve as claimed in claim 13, in admixture with at least one formulating agent.

* * * * *